United States Patent [19]

Kojima et al.

[11] 4,348,359
[45] Sep. 7, 1982

[54] DEVICE FOR DETERMINING VARIOUS TYPES OF TRACE NITROGEN

[75] Inventors: Tomonori Kojima; Yasumitsu Katsuno, both of Kita-Kyushu, Japan

[73] Assignee: Mitsubishi Chemical Industries, Limited, Tokyo, Japan

[21] Appl. No.: 270,231

[22] Filed: Jun. 4, 1981

[30] Foreign Application Priority Data

Jul. 16, 1980 [JP] Japan ................................. 55-97066
Jul. 16, 1980 [JP] Japan ................................. 55-97067
Jul. 16, 1980 [JP] Japan ................................. 55-97068

[51] Int. Cl.³ ...................... G01N 31/10; G01N 31/16
[52] U.S. Cl. ................................. 422/76; 204/195 T; 204/1 T; 422/78; 422/80; 23/232 E
[58] Field of Search .................... 422/76, 78, 80; 23/232 R, 906, 928; 204/195 T, 1 N

[56] References Cited

U.S. PATENT DOCUMENTS 2,998,305  8/1961  Wilson ............................. 422/76
3,461,042  8/1969  Martin et al. .................... 204/1 N
3,497,322  2/1970  Boys ................................ 204/1 N
4,026,665  5/1977  Mansfield et al. ............... 422/78
4,081,345  3/1978  Tölg et al. ..................... 204/195 T
4,197,177  4/1980  Proctor ........................... 204/1 N Primary Examiner—Michael S. Marcus
Attorney, Agent, or Firm—Oblon, Fisher, Spivak, McClelland & Maier

[57] ABSTRACT

An apparatus for determining various types of trace nitrogen having a measuring system which includes, a reaction section with a catalyst for reduction, an acidic gas removal section with a solid alkaline substance, heating sections for heating the reaction section and the acidic gas removal section, a coulometric titration section, and at least one distillation system.

12 Claims, 3 Drawing Figures

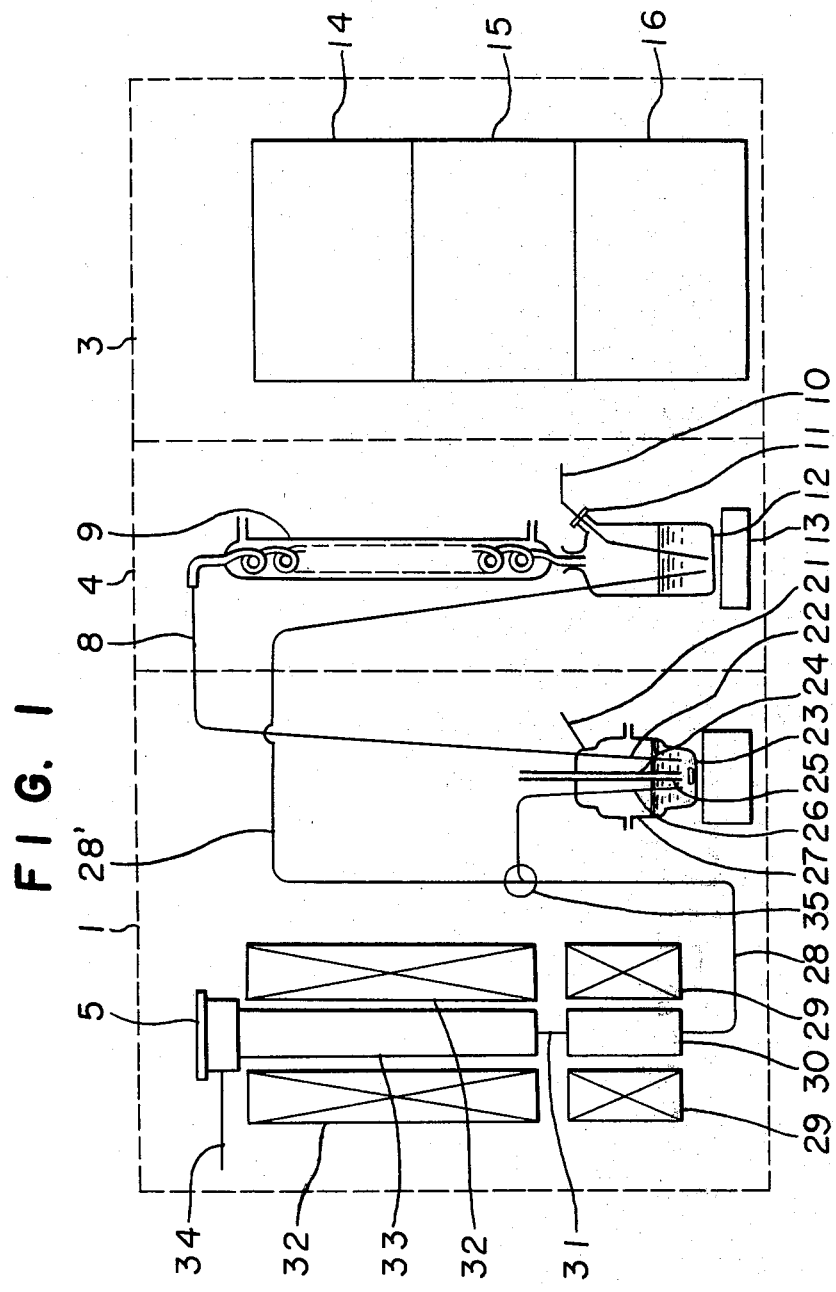

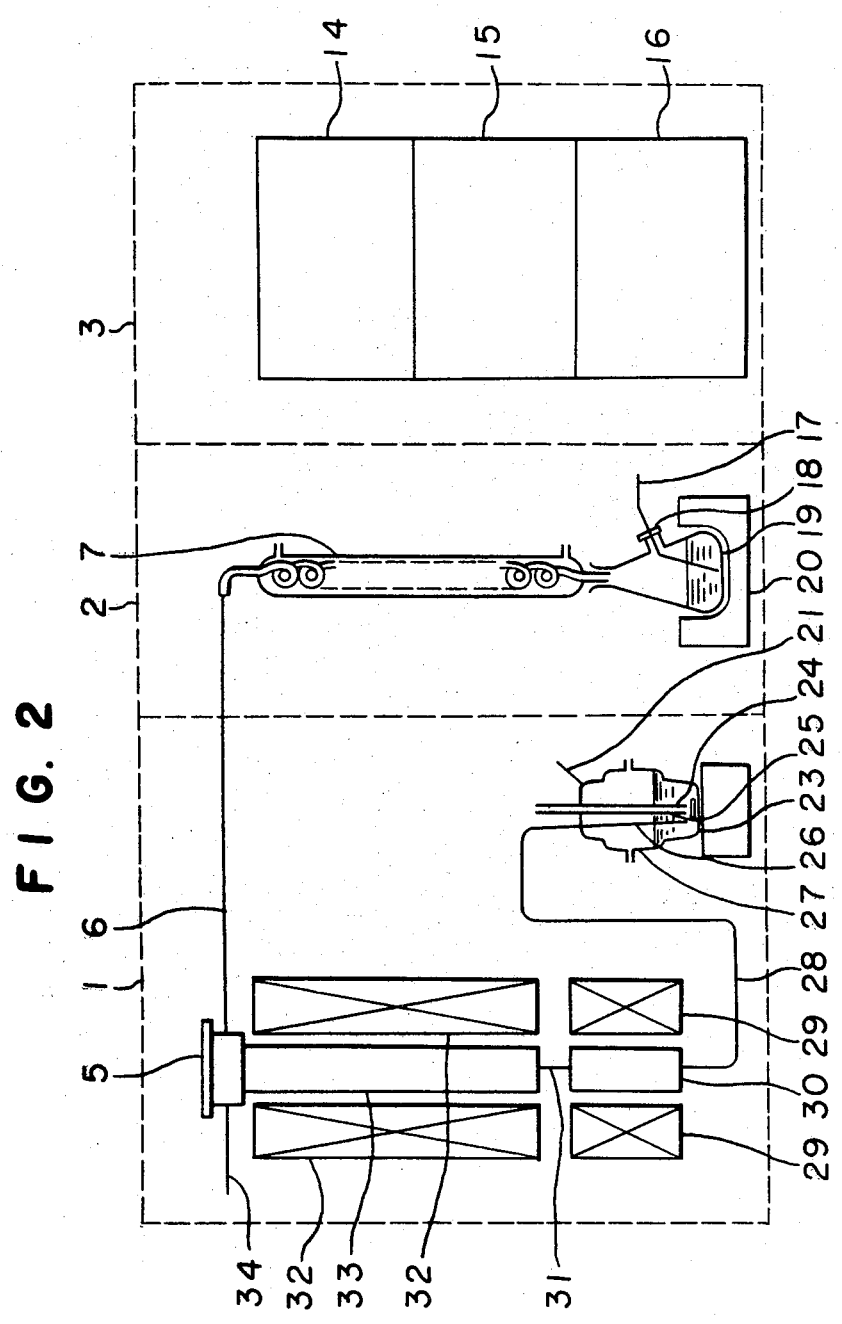

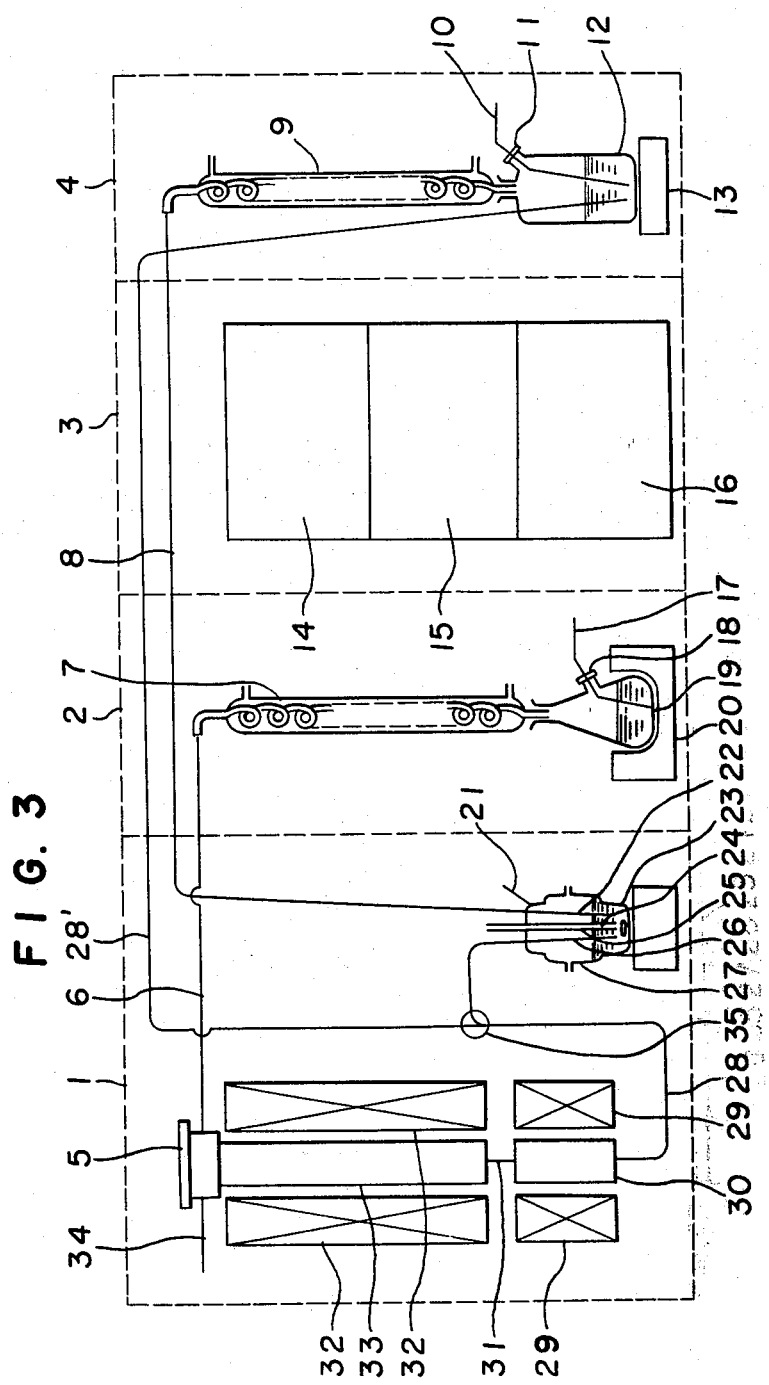

DEVICE FOR DETERMINING VARIOUS TYPES OF TRACE NITROGEN

BACKGROUND OF THE INVENTION

1. Field of the Invention

The present invention relates to a device for determining various types of trace nitrogen, and particularly to a device for separating and quantitatively measuring the contents of ammonium type nitrogen, nitrous type nitrogen, nitric type nitrogen and organic type nitrogen respectively.

2. Description of the Prior Art

Recently there have been serious problems arising out the nitrogen content and composition in environmental water such as river water, lake or pond water, and sea water, or waste water such as industrial waste water, process waste water, and hygenic waste water, which are said to cause a nutrient enrichment phenomenon for waters. Types of nitrogen contained in these water may be classified into four categories of an ammonium type, a nitrous type, a nitric type and an organic type. It is important to know the contents of the respective types of nitrogen to cope with the pollution problems of waste water.

There has hitherto been proposed a device for determining various types of trace nitrogen, in which two reaction tubes are provided and helium is used as carrier gas. In the first reaction tube, ammonium type nitrogen in the sample water is oxydized to nitrogen gas by a hypobromic ion containing reaction liquid, and after completely removing the accompanying moisture, quantitatively analyzed by gas chromatography. In the second reaction tube, nitrous type nitrogen in the sample water was reduced to nitrogen gas by an amidosulfonic acid reaction liquid, and after completely removing the accompanying moisture, quantitatively analized by gas chromatography. Nitric type nitrogen is reduced to nitrous ion by zinc powder and then analyzed by the above-mentioned second method. However, with this device, it is necessary to remove the nitrogen gas dissolved in each reaction liquid and sample water completely in advance, and it is further necessary that after the reduction to nitrogen gas, the accompanying moisture must completely be removed. Thus, such a device has drawbacks that the preliminary treatment is time-consuming, and the operation is cumbersome.

SUMMARY OF THE INVENTION

An object of the present invention is to provide a device for determining various types of trace nitrogen, which has no such drawbacks. Thus, the present invention provides a device for determining various types of trace nitrogen, which comprises the following measuring system, distillation system A and/or distillation system B:

(a) a measuring system which comprises
(1) a reaction section comprising a cylindrical reaction tube having a sample inlet and a hydrogen gas supplying tube at one end, and a gas outlet at the other end, and packed therein with a catalyst for reduction,
(2) an acidic gas removal section comprising a container having a gas inlet and a gas outlet, and packed therein with a solid alkaline substance,
(3) heating sections for heating the reaction section and the acidic gas removal section, and
(4) a coulometric titration section comprising a gas supplying tube, a gas outlet, electrolytic electrodes, termination point detecting electrodes, and an electrolytic cell,
the reaction section and the acidic gas removal section being accommodated in the respective heating sections, the gas outlet of the reaction section being connected to the gas inlet of the acidic gas removal section, the gas outlet of the acidic gas removal section being connected with the gas supplying tube of the coulometric titration section, and said gas supplying tube being open in the vicinity of the bottom within the electrolytic cell, (b) a distillation system B which comprises
(1) a distillation vessel having a sample inlet, a carrier gas supplying tube, and a gas outlet, and made of an acid resistant material, and
(2) a reflux condenser, the carrier gas supplying tube being open in the vicinity of the bottom of the distillation vessel, the lower end of the reflux condenser being connected with the gas outlet of the distillation vessel and the upper end thereof being connected with said reaction section in the vicinity of the sample inlet, and (c) a distillation system A which comprises
(1) a distillation vessel having a sample inlet, a carrier gas supplying tube and a gas outlet, and made of an alkali resistant material,
(2) a reflux condenser,
the carrier gas supplying tube being open in the vicinity of the bottom in the distillation vessel, the lower end of the reflux condenser being connected with the gas outlet of the distillation vessel, and the upper end thereof being connected with the gas supplying tube of said coulometric titration section.

BRIEF DESCRIPTION OF THE DRAWINGS

FIGS. 1 to 3 illustrate preferred embodiments of the device according to the present invention.

DETAILED DESCRIPTION OF THE PREFERRED EMBODIMENTS

Now, the present invention will be described with reference to the drawings. FIGS. 1 to 3 illustrate preferred embodiments of the device according to the present invention. In the FIGS., reference numeral (1) is a measuring system, numeral (2) is a distillation system B, numeral (3) is a control system, and numeral (4) is a distillation system A. Numerals (12) and (19) are distillation vessels numeral (23) is a coulometric titration section, numerals (29) and (32) are heating sections, numeral (30) is an acidic gas removal section, and numeral (33) is a reaction section.

The measuring system 1 comprises the reaction section (33) for reducing the nitrogen compounds in a sample and converting them into ammonia, the acidic gas removal section (30) for removing the acidic gas in the converted gas, and the coulometric titration section (23) for quantitatively measuring the ammonia content.

The reaction section (33) comprises a cylindrical reaction tube having a sample inlet (5) and a hydrogen gas supplying tube (34) at one end, a gas outlet (31) at another end, and packed therein with a metal catalyst composed of metal particles such as nickel or copper, or inert particles such as pumice or alumina, which are coated with such metals. The size of the catalyst particles is usually within a range from 0.5 to 15 mm although it may depend upon the size of the reaction tube. It is preferred that the catalyst is packed as a mixture of catalyst particles with a heat resistant inert substance such as quartz, asbestos or alumina. The reaction section (33) is accommodated in the heating section (32) such as an electric furnace with an electric heating wire incorporated therein, and maintained at a high temperature within a range from 300° to 600° C.

The acidic gas removal section (30) is adapted to remove an acidic gas such as hydrogen sulfide accompanying the gas discharged from the reaction section, and it usually comprises a container having an gas inlet and a gas outlet and packed with alkaline absorbing chemicals composed of particles of one or more selected from oxides or hydroxides of alkali metals and alkaline metals having a particle size within a range of from 1 to 7 mm. As specific examples of the alkaline absorbing chemicals, there may be mentioned a mixture (soda lime) of sodium hydroxide and calcium oxide, a mixture of calcium hydroxide and calcium oxide, a mixture of sodium hydroxide and α-alumina, and a mixture of sodium hydroxide, potassium carbonate and asbestos.

The acidic gas removal section (30) is accommodated in the heating section (29) which is similar to the heating section (32), and maintained at a temperature within a range from ambient temperature 20° C. to 300° C.

The coulometric titration section (23) is adapted to quantitatively measure ammonia content in the gas discharged from the acidic gas removal section, and it comprises an electrolytic cell (27) having a ground fitting lid, and electrolytic electrodes (24), detecting electrodes (25), gas supplying tubes (22), (26), and a gas discharge tube (21) disposed in said electrolytic cell. Each of the electrodes (24), (25), and the gas supplying tubes (22), (26) is disposed so that the lower end is located at a position to be immersed in the electrolytic solution.

The distillation system B (2) is applied to dispel nitrous type nitrogen in the sample in a form of nitrogen monoxide gas or nitrogen dioxide gas, and it comprises a distillation vessel (19) having a sample inlet (18), a carrier gas supplying tube (17), and a gas outlet, a reflux condenser (7), and a heater (20). The carrier gas supplying tube (17) is open in the vicinity of the bottom in the distillation vessel (19), and the opening end should preferably be provided with a multiperforated plate. Since an aqueous solution containing from 30 to 80% by weight, preferably from 30 to 50% by weight, of a non-volatile strong acid such as sulfuric acid or phosphoric acid, is placed in the distillation vessel (19), it is desirable that the distillation vessel is made of an acid resistant material such as glass or ceramics. The reflux condenser (7) is preferably provided with an obstacle in the gas flow passway so as to prevent an escape of a mist. Usually a spiral tube type is used. A straight tube type may be used with fillers inserted therein.

The lower opening end of the reflux condenser (7) is connected with the gas outlet of the distillation vessel (19), and the upper opening end is connected, via a conduit (6), with the abovementioned reaction section (33) in the vicinity of the sample inlet (5). The distillation vessel (19) is heated to a temperature of from 70° C. to the boiling temperature of the liquid, preferably from 80° to 90° C. by the heater (20).

The distillation system A (4) is adapted to dispel ammonium type nitrogen in the sample in a form of ammonia gas, and it comprises a distillation vessel (12) having a sample inlet (11), a carrier gas supplying tube (10) and a gas outlet, a reflux condenser (9) and a heater (13). The carrier gas supplying tube (10) is open in the vicinity of the bottom of the distillation vessel (12), and the opening end is preferably provided with a multi-perforated plate. Since an aqueous solution containing from 20 to 50% by weight, preferably from 20 to 40% by weight of a strong alkali such as sodium hydroxide or potassium hydroxide, is placed in the distillation vessel (12), it is desirable that the distillation vessel (12) is made of an alkali resistant material such as a high nickel alloy steel or ceramics. The reflux condenser (9) is a type similar to the reflux condenser (7), and its lower opening end is connected with the gas outlet of the distillation vessel (12), and its upper opening end is connected, via a conduit (8), with the gas supplying tube (22) of the above-mentioned coulometric titration section (23). The distillation vessel (12) is heated at a temperature of from 70° C. to the boiling point of the liquid, preferably from 100° C. to the boiling temperature of the liquid, by the heater (13).

The control system (3) usually comprises a coulometric titration control component (14), a temperature control component (15) and a gas flow rate control component (16). The coulometric titration control component (14) is applied to amplify an electric signal corresponding to the hydrogen ion concentration detected by the detecting electrodes (25), convert it to an electric current output proportional to the deviation from the pH value at the termination point, and supply it as the electrolytic current to the electrolytic electrodes (24).

On the other hand, this electrolytic current is, if necessary, adjusted by deduction of the blank current to a deducted current, and after carrying out conversion to the analytical unit and corrective operations by e.g. a coefficient of the amount of the sample for representing the proportion to the sample, integrated to represent a direct analytical value corresponding to the quantity of electricity.

The temperature control component (15) is applied to adjust the temperatures of the heating sections (19), (32) and heaters (13), (20) to the set levels.

The gas flow rate control component (16) is applied to adjust the flow rates of the hydrogen gas supplied from the hydrogen gas supplying tube (34) and a carrier gas such as hydrogen gas, nitrogen gas, or argon gas, supplied from the carrier gas supplying tubes (10), (17), to the set levels. The flow rates of these gases are normally within a range from 200 to 700 ml./min., preferably from 400 to 500 ml./min.

Now, the operation of the device of the present invention having the above construction, will be described with respect to the case where the device is used for carrying out an analysis of water containing a trace of nitrogen compounds. Firstly, for the determination of a total amount of nitrogen, a set amount of the sample water is introduced from the sample inlet (5) of the measuring system (1). The sample water thus introduced is carried by the hydrogen gas supplied from the hydrogen gas supplying tube (34), and at the reaction section (33), all nitrogen compounds are reduced to ammonia. The ammonia gas thus formed is, together with the hydrogen gas, introduced through a conduit (31) into the acidic gas removal section (30), where the accompanying acidic gas is removed. Then, the ammonia gas is led to the electrolytic cell (27) through conduits (28) and (26), or, in the devices shown in FIGS. 1 and 3, from a conduit (28′), via the distillation vessel (12) and a conduit (8) or (22), by switching over a three way switching-valve (35), and absorbed by the electrolytic solution such as an aqueous solution containing 1% of sodium sulfate, whereupon the coulometric titration is carried out. The reason for passing the gas through the distillation vessel (12), is to remove the moisture content from the gas. The results obtained by the titration will be shown on the panel of the coulometric titration control component (14). The amount of the sample water to be introduced, varies depending upon the amount of nitrogen compounds contained. However, usually it is within a range from 5 to 500μl, or, in the case where the moisture is removed by passing through the distillation vessel (12), it is possible to increase the amount to a level of 5 ml. A single measurement operation can be completed within 4 to 8 minutes.

Next, in the case where nitrous type nitrogen is measured by the device shown in FIG. 2 or 3, a set amount of the sample water is introduced from the sample inlet (18) of the distillation system B(2). The nitrous type nitrogen in the sample water thus introduced, is converted to nitrogen monoxide or nitrogen dioxide, and carried with a carrier gas introduced from the carrier gas supplying tube (17). After removal of most of the accompanying moisture by the reflux condenser (7), the gas is led through a conduit (6) to the reaction section (33), where the gas is reduced to ammonia in the same manner as described above and subjected to the coulometric titration. In this case, nitric type nitrogen remains in the solution in the distillation vessel (19). The amount of the sample water to be introduced, varies depending upon the amount of nitrous type nitrogen compounds, but is normally within a range of 5μl to 5 ml. A single measurement operation can be completed within 6 to 8 minutes.

For the measurement of nitric type nitrogen, a sample water is preliminarily subjected to reduction treatment to reduce the nitric type nitrogen to nitrous ions, and then the measurement is carried out in accordance with the above-mentioned method for measuring nitrous type nitrogen. A single measurement operation can be completed within 10 to 15 minutes. The reduction treatment of the sample water may be carried out, for instance, by a method of JIS-K 0104. For instance, 80 ml. of a sample water is placed in a volumetric flask of 100 ml., 15 ml. of a neutral buffer solution is added and mixed, and then, 0.5 g. of zinc powder is added and water is immediately added to the level of the reference line. After mixing for about one minute, unreacted zinc powder is separated by filtration, and the filtrate is used as the sample.

The measurement of ammonium type nitrogen is carried out by the device shown in FIG. 1 or 3, and a set amount of the sample water is introduced from the sample inlet (11) of the distillation system A (4). The ammonium type nitrogen in the sample water thus introduced, is converted to ammonia gas, and carried with a carrier gas introduced from the carrier gas supplying tube (10). After removal of most of the accompanying moisture by the reflux condenser (9), the ammonia gas is led through conduits (8) and (22) to the electrolytic cell (27) of the coulometric titration section (23), whereupon it is subjected to the coulometric titration in accordance with the abovementioned method. The amount of the sample water to be introduced, varies depending upon the amount of the nitrogen compounds contained, but is normally within a range from 5μl to 5 ml. A single measurement operation can be completed within 6 to 8 minutes.

The content of organic type nitrogen is obtainable by deducting, by calculation, the analytical values of the nitrous type nitrogen, the nitric type nitrogen and the ammonium type nitrogen from that of the total nitrogen measured by the above-mentioned method.

As described in detail hereinabove, the device of the present invention comprises the distillation system B (2) and/or the distillation system A (4), which are not subject to influences of water, in combination with the measuring system (1), whereby it is possible to measure accurately and within a short period of time, various types of nitrogen compounds separately to the extent of a trace as low as 0.002 ppm, by varying the amounts of the samples to be introduced. Thus, the device of the present invention is extremely useful for a total nitrogen determination and a determination of various types of nitrogen, in connection with environmental water, waste water, agricultural products, food products or pharmaceutical products.

We claim:

1. A device for determining various types of trace nitrogen, which comprises the following measuring system and distillation system (A):
   (a) a measuring system which comprises
   (1) a reaction section comprising a cylindrical reaction tube having a sample inlet and a hydrogen gas supplying tube at one end, and a gas outlet at the other end, and packed therein with a catalyst for reduction,
   (2) an acidic gas removal section comprising a container having a gas inlet and a gas outlet, and packed therein with a solid alkaline substance,
   (3) heating sections for heating the reaction section and the acidic gas removal section, and
   (4) a coulometric titration section comprising gas supplying tube means, a gas outlet, electrolytic electrodes, termination point detecting electrodes, and an electrolytic cell,
   the reaction section and the acidic gas removal section being accommodated in the respective heating sections, the gas outlet of the reaction section being connected with the gas inlet of the acidic gas removal section, the gas outlet of the acidic gas removal section being connected with the gas supplying tube means of the coulometric titration section, and said gas supplying tube means being open in the vicinity of the bottom in the electrolytic cell, and
   (b) a distillation system A which comprises
   (1) a distillation vessel having a sample inlet, a carrier gas supplying tube and a gas outlet, and made of an alkali resistant material, and
   (2) a reflux condenser, said carrier gas supplying tube being open in the vicinity of the bottom in the distillation vessel, the lower end of the reflux condenser being connected with the gas outlet of the distillation vessel and the upper end thereof being connected with the gas supplying tube means of said coulometric titration section.

2. A device for determining various types of trace nitrogen, which comprises the following measuring system and distillation system B:
   (a) a measuring system which comprises
   (1) a reaction section comprising a cylindrical reaction tube having a sample inlet and a hydrogen gas supplying tube at one end, and a gas outlet at the other end, and packed therein with a catalyst for reduction, (2) an acidic gas removal section comprising a container having a gas inlet and a gas outlet, and packed therein with a solid alkaline substance,
(3) heating sections for heating the reaction section and the acidic gas removal section, and
(4) a coulometric titration section comprising a gas supplying tube, a gas outlet, electrolytic electrodes, termination point detecting electrodes, and an electrolytic cell, the reaction section and the acidic gas removal section being accommodated in the respective heating sections, the gas outlet of the reaction section being connected with the gas inlet of the acidic gas removal section, the gas outlet of the acidic gas removal section being connected with the gas supplying tube of the coulometric titration section, and said gas supplying tube being open in the vicinity of the bottom in the electrolytic cell, and (b) a distillation system B which comprises
(1) a distillation vessel having a sample inlet, a carrier gas supplying tube and a gas outlet, and made of an acid resistant material, and
(2) a reflux condenser, the carrier gas supplying tube is open in the vicinity of the bottom in a distillation vessel the lower end of the reflux condenser being connected with the gas outlet of the distillation vessel and the upper end thereof being connected to said reaction section in the vicinity of the sample inlet.

3. A device for determining various types of trace nitrogen, which comprises the following measuring system, distillation system B and distillation system A:
(a) a measuring system which comprises
(1) a reaction section comprising a cylindrical reaction tube having a sample inlet and a hydrogen gas supplying tube at one end, and a gas outlet at the other end, and packed therein with a catalyst for reduction,
(2) an acidic gas removal section comprising a container having a gas inlet and a gas outlet, and packed therein with a solid alkaline substance,
(3) heating sections for heating the reaction section and the acidic gas removal section, and
(4) a coulometric titration section comprising gas supplying tube means, a gas outlet, electrolytic electrodes, termination point detecting electrodes and an electrolytic cell, the reaction section and the acidic gas removal section being accommodated in the respective heating sections, the gas outlet of the reaction section being connected with the gas inlet of the acidic gas removal section, the gas outlet of the acidic gas removal section being connected with the gas supplying tube means of the coulometric titration section, and said gas supplying tube means being open in the vicinity of the bottom in the electrolytic cell, (b) a distillation system B which comprises
(1) a distillation vessel having a sample inlet, a carrier gas supplying tube and a gas outlet, and made of an acid resistant material, and
(2) a reflux condenser, the carrier gas supplying tube being open in the vicinity of the bottom in the distillation vessel, the lower end of the reflux condenser being connected with the gas outlet of the distillation vessel and the upper end thereof being connected with said reaction section in the vicinity of the sample inlet, and
(c) a distillation system A which comprises (1) a distillation vessel having a sample inlet, a carrier gas supplying tube and the gas outlet, and made of an alkali resistant material, and
(2) a reflux condenser, the carrier gas supplying tube being open in the vicinity of the bottom in the distillation vessel, the lower end of the reflux condenser being connected with the gas outlet of the distillation vessel, and the upper end thereof being connected with the gas supplying tube means of said coulometric titration section.

4. A device for determining various types of trace nitrogen, which comprises the following measuring system and distillation system A:
(a) a measuring system which comprises
(1) a reaction section comprising a cylindrical reaction tube having a sample inlet and a hydrogen gas supplying tube at one end, and a gas outlet at the other end, and packed therein with a catalyst for reduction,
(2) an acidic gas removal section comprising a gas inlet and a gas outlet, and packed therein with a solid alkaline substance,
(3) heating sections for heating the reaction section and the acidic gas removal section, and
(4) a coulometric titration section comprising a gas supplying tube, a gas outlet, electrolytic electrodes, termination point detecting electrodes, and an electrolytic cell, the reaction section and the acidic gas removal section being accommodated in the respective heating section, the gas outlet of the reaction section being connected with the gas inlet of the acidic gas removal section, the gas outlet of the acidic gas removal section being connected with the gas supplying tube of the distillation vessel of the below-mentioned distillation system A, and the gas supplying tube of the coulometric titration section being open in the vicinity of the bottom in the electrolytic cell, and (b) a distillation system A which comprises
(1) a distillation vessel having a sample inlet, a gas supplying tube, a carrier gas supply tube, and a gas outlet, and made of an alkali resistant material, and
(2) a reflux condenser, the gas supplying tube and the carrier gas supplying tube of the distillation vessel being open in the vicinity of the bottom in the distillation vessel, the lower end of the reflux condenser being connected with the gas outlet of the distillation vessel, and the upper end thereof being connected to the gas supplying tube of said coulometric titration section.

5. A device for determining various types of trace nitrogen, which comprises the following measuring system, distillation system B and distillation system A:
(a) a measuring system which comprises
(1) a reaction section comprising a cylindrical reaction tube having a sample inlet and a hydrogen gas supplying tube at one end, and a gas outlet at the other end, and packed therein with a catalyst for reduction,
(2) an acidic gas removal section comprising a container having a gas inlet and a gas outlet, and packed therein with a solid alkaline substance,
(3) heating sections for heating the reaction section and the acidic gas removal section, and
(4) a coulometric titration section comprising a gas supplying tube, a gas outlet, electrolytic electrodes, termination point detecting electrodes, and an electrolytic cell, the reaction section and the acidic gas removal section being accommodated in the respective heating section, the outlet of the reaction section being connected with the gas inlet of the acidic gas removal section, the gas outlet of the acidic gas removal section being connected with the gas supplying tube of the distillation vessel of the below-mentioned distillation system A, and the gas supplying tube of the coulometric titration section being open in the vicinity of the bottom in the electrolytic cell, (b) a distillation system B which comprises
  (1) a distillation vessel having a sample inlet, a carrier gas supplying tube, and a gas outlet, and made of an acid resistant material,
  (2) a reflux condenser, the carrier gas supplying tube being open in the vicinity of the bottom in the distillation vessel, the lower end of the reflux condenser being connected with the gas outlet of the distillation vessel and the upper end thereof being connected with said reaction section in the vicinity of the sample inlet, (c) a distillation system A which comprises
  (1) a distillation vessel having a sample inlet, a gas supplying tube, a carrier gas supplying tube and a gas outlet, and made of an alkali resistant material, and
  (2) a reflux condenser, the gas supplying tube and the carrier gas supplying tube of the distillation vessel being open in the vicinity of the bottom in the distillation vessel, the lower end of the reflux condenser being connected with the gas outlet of the distillation vessel, and the upper end thereof being connected with the gas supplying tube of said coulometric titration section.

6. The device as claimed in any one of claims 1 to 5, wherein the catalyst for reduction comprises nickel metal particles.

7. The device as claimed in any one of claims 1 to 5, wherein the catalyst for reduction is packed in the reaction section in a form of a mixture with a heat resistant, inert substance.

8. The device as claimed in any one of claims 1 to 5, wherein the solid alkaline substance is one or more selected from the group consisting of oxides and hydroxides of alkali metals and alkaline earth metals.

9. The device as claimed in any one of claims 1 to 5, wherein the reaction section is maintained at a temperature of from 300° to 600° C. by the heating section.

10. The device as claimed in any one of claims 1 to 5, wherein the acidic gas removal section is maintained at a temperature of from 20° to 300° C.

11. The device as claimed in claims 1, 3 or 5, wherein the alkali resistant material is nickel alloy steel or ceramics.

12. The device as claimed in claims 2, 3 or 5, wherein the acid resistant material is glass, or ceramics.

* * * * *